United States Patent
Chiang

(10) Patent No.: US 11,147,470 B2
(45) Date of Patent: Oct. 19, 2021

(54) PHYSIOLOGICAL SIGNAL WIRELESS TRANSMISSION SYSTEM AND THE OPERATING METHOD THEREOF

(71) Applicant: Orion Biotech Inc., Taipei (TW)

(72) Inventor: Ming-Fu Chiang, Taipei (TW)

(73) Assignee: ORION BIOTECH INC., Taipei (TW)

( * ) Notice: Subject to any disclaimer, the term of this patent is extended or adjusted under 35 U.S.C. 154(b) by 203 days.

(21) Appl. No.: 16/191,431

(22) Filed: Nov. 14, 2018

(65) Prior Publication Data
US 2020/0146590 A1 May 14, 2020

(51) Int. Cl.
*A61B 5/07* (2006.01)
*H02J 50/20* (2016.01)
(Continued)

(52) U.S. Cl.
CPC .......... *A61B 5/076* (2013.01); *A61B 5/02055* (2013.01); *A61B 5/7425* (2013.01); *H01Q 1/24* (2013.01); *H01Q 1/273* (2013.01); *H02J 50/20* (2016.02); *A61B 5/01* (2013.01); *A61B 5/021* (2013.01); *A61B 5/024* (2013.01); *A61B 5/031* (2013.01); *A61B 5/055* (2013.01);
(Continued)

(58) Field of Classification Search
CPC ... A61B 5/076; A61B 5/02055; A61B 5/7425; A61B 5/01; A61B 5/021; A61B 5/024; A61B 5/031; A61B 5/055; A61B 5/08; A61B 5/14542; H02J 50/20; H02J 7/025; H01Q 1/24; H01Q 1/273
USPC .......................................................... 600/301
See application file for complete search history.

(56) References Cited

U.S. PATENT DOCUMENTS

2008/0234598 A1\* 9/2008 Snyder .................. A61B 5/374
600/545
2010/0256481 A1 10/2010 Mareci et al.
(Continued)

FOREIGN PATENT DOCUMENTS

CN 101856222 A 10/2010
TW I589086 B 6/2017

OTHER PUBLICATIONS

Bai-Yu Wu, "Leveraging the 5.8GHz High-Frequency Band, RF Wireless Charging Systems Have Evolved Again", Micro Electronics, Aug. 2, 2018, Cite Publishing LTD.

*Primary Examiner* — Erin M Piateski
(74) *Attorney, Agent, or Firm* — Cheng-Ju Chiang

(57) ABSTRACT

The present invention discloses a physiological signal wireless transmission system which is compatible with a magnetic resonance system. The physiological signal wireless transmission system comprises an implantable sensing device, and a power relay device wirelessly connected to the implantable sensing device. The implantable sensing device comprises a sensing module including at least one sensor, a data transmission module coupled to the sensing module, and a power receiving module coupled to the sensing module and the data transmission module. On the other hand, the power relay device comprising a data transmission antenna wirelessly connected to the data transmission module, a first microprocessor connected to the data transmission antenna, a display module connected to the first microprocessor, a power transmitting antenna wirelessly connected to the power receiving module, and a power emitting module coupled to the power transmitting antenna.

9 Claims, 8 Drawing Sheets

(51) Int. Cl.
  *A61B 5/0205*  (2006.01)
  *A61B 5/00*    (2006.01)
  *H01Q 1/27*    (2006.01)
  *H01Q 1/24*    (2006.01)
  *A61B 5/055*   (2006.01)
  *A61B 5/021*   (2006.01)
  *A61B 5/024*   (2006.01)
  *A61B 5/01*    (2006.01)
  *A61B 5/08*    (2006.01)
  *A61B 5/145*   (2006.01)
  *A61B 5/03*    (2006.01)
  *H02J 7/02*    (2016.01)

(52) U.S. Cl.
  CPC ............ *A61B 5/08* (2013.01); *A61B 5/14542* (2013.01); *H02J 7/025* (2013.01)

(56) References Cited

U.S. PATENT DOCUMENTS

| | | | | |
|---|---|---|---|---|
| 2012/0265028 A1* | 10/2012 | Hughes | ............... | A61B 5/1117 600/301 |
| 2018/0294676 A1* | 10/2018 | Davlantes | ........... | G01R 31/2822 |
| 2019/0247669 A1* | 8/2019 | Nielsen | ................ | H02J 50/80 |
| 2020/0119591 A1* | 4/2020 | Arnitz | ................... | H02J 50/80 |

* cited by examiner

20

130

PHYSIOLOGICAL SIGNAL WIRELESS TRANSMISSION SYSTEM AND THE OPERATING METHOD THEREOF

TECHNICAL FIELD

The present invention relates to a physiological signal wireless transmission system, particularly, to a physiological signal wireless transmission system which can sense intracranial pressure (ICP) and be compatible with magnetic resonance (MR), and the operating method thereof.

BACKGROUND OF RELATED ARTS

Magnetic resonance imaging (MRI), when judged by trained physicians, can produce useful diagnostic information. This can also be used for imaging during the interventional treatment using MR compatible system. However, MRI is not suitable for examining patients embedded with electronic implants, conductive implants, or metal object with ferromagnetic material.

At present, the implantable sensing receiver must disconnect all cables and patient monitoring equipment before entering the magnetic resonance (MR) system, and special fixed embedding apparatus is provided to ensure the safety of the patient during the MRI examination. For example, sensor wires with several meters and electrical connectors must be placed in a specific geometry to minimize the possibility of the sensor being heated by a strong magnetic field.

Rechargeable implantable sensor or wireless transmission sensor is an active implant, which means that the device contains magnetic conductive metal material or rechargeable batteries. In serious case, the implant may be moving or induce parabolic acceleration motion in the human body.

SUMMARY

To resolve the drawbacks of the prior arts, the present invention discloses a physiological signal wireless transmission system compatible with the magnetic resonance (MR) system comprising an implantable sensing device and a power relay device wirelessly coupled to the implantable sensing device.

The implantable sensing device includes a sensing module having at least one sensor to sense at least one physiological signal; a data transmission module coupled to the sensing module to transmit the at least one physiological signal; a power receiving module coupled to the sensing module and the data transmission module to provide a working voltage to the sensing module and the data transmission module.

In addition, the power relay device includes a data transceiver antenna wirelessly coupled to the data transmission module to receive and transmit the at least one physiological signal; a first microprocessor coupled to the data transceiver antenna; a display module coupled to the first microprocessor to display the at least one physiological signal; a power emitting antenna wirelessly coupled to the power receiving module; and a power emitting module coupled to the power emitting antenna to generate a radio frequency signal with 815 MHz to 5.8 GHz.

Furthermore, the physiological signal wireless transmission system further comprises an external monitoring device wirelessly coupled to the power relay device. The external monitoring device comprises a data receiving unit wirelessly coupled to the data transceiver antenna to receive the at least one physiological signal; a second microprocessor coupled to the data receiving unit; and a display unit coupled to the second microprocessor to display the at least one physiological signal.

Embodiments of the invention are illustrated by way of example, and not by way of limitation, in the figures of the accompanying drawings in which like reference numerals refer to similar elements:

DETAILED DESCRIPTION OF THE INVENTION

In order to understand the technical features and practical efficacy of the present invention and to implement it in accordance with the contents of the specification, hereinafter, preferred embodiments of the present invention will be described in detail with reference to the accompanying drawings.

The invention proposes a physiological signal wireless transmission system compatible with the magnetic resonance (MR) system. The physiological signal wireless transmission system removes batteries or magnetic conductive metals from traditional sensing devices and provides power energy for system signal monitoring and data transmission by means of wireless charging to avoid the risk caused by current magnetic field excited from the sensing devices when magnetic resonance scanning is performed.

Figure 1:
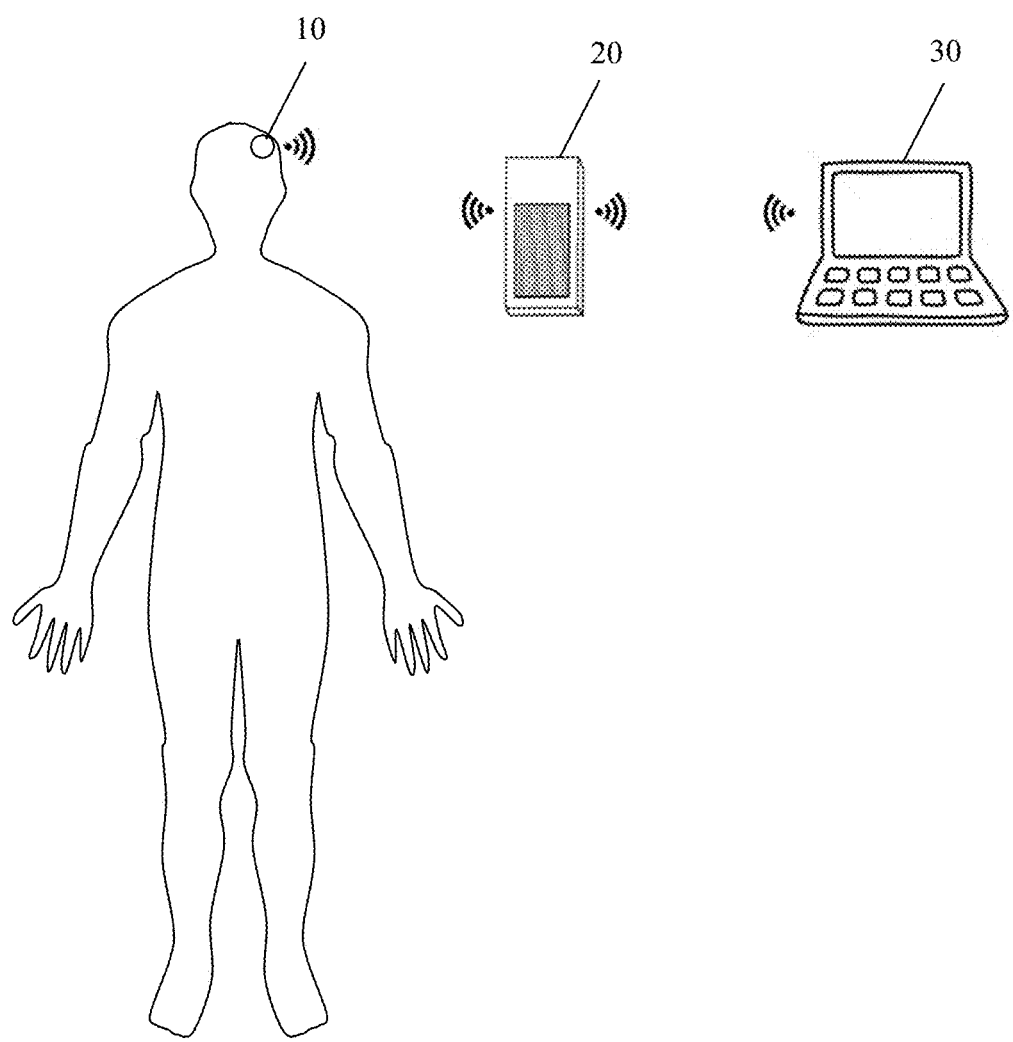
FIG. 1 is a schematic diagram of the physiological signal wireless transmission system of an embodiment of the present invention.

Please refer to FIG. 1, it illustrates a schematic diagram of the physiological signal wireless transmission system of one embodiment of the invention. As shown in FIG. 1, the physiological signal wireless transmission system 1 of the present embodiment comprises an implantable sensing device 10 and a power relay device 20 wirelessly connected with the implantable sensing device 10. The physiological signals of the human body are sensed by the implantable sensing device 10 and the signals are transmitted to the power relay device 20 for displaying on the screen. On the other hand, the power relay device 20 can also wirelessly and non-contactly provide power energy needed for signal monitoring and data transmission of the implantable sensing device 10.

In addition, the physiological signal wireless transmission system 1 of the present embodiment further includes an external monitoring device 30 wirelessly connected to the power relay device 20. The external monitoring device 30 may remotely receive the physiological signal transmitted by the power relay device 20 and display it on the screen so that the remote operator can also monitor numerical value of the physiological signal of the human body in real time.

The system architecture and connection relationship of the implantable sensing device 10 of the present embodiment will be explained below.

Figure 2:
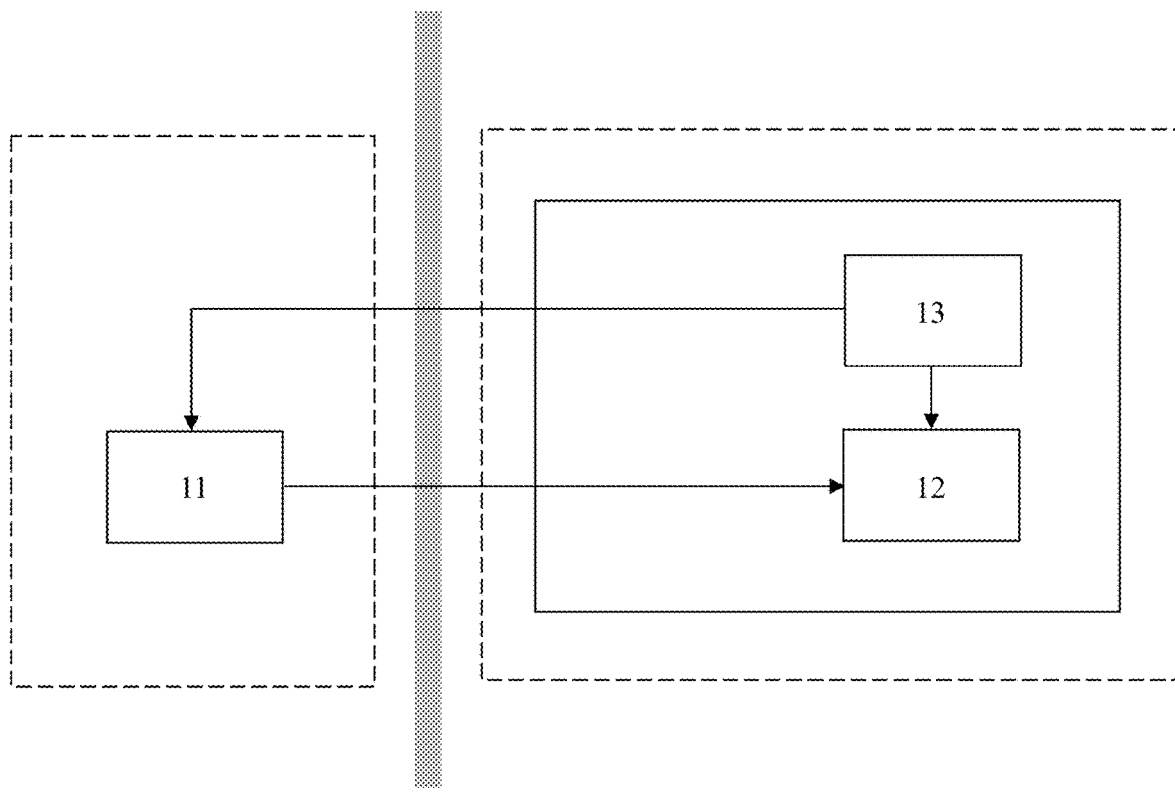
FIG. 2 is a schematic diagram of the implantable sensing device in accordance with one embodiment of the present invention.

First of all, please refer to FIG. 2, it illustrates a schematic diagram of the implantable sensing device of one preferred embodiment of the invention. As shown in FIG. 2, the implantable sensing device 10 of the present embodiment includes a sensing module 11 implanted into the human body, a data transmission module 12 connected with the sensing module 11, and a power receiving module 13 connected with the sensing module 11 and the data transmission module 12, respectively.

The sensing module 11 includes at least one sensor (not shown) for sensing at least one physiological signal of the human body, and the at least one sensor may be an intracranial pressure (ICP) sensor for sensing intracranial pressure, a blood pressure sensor for sensing systolic/diastolic pressure of human body, a blood oxygen sensor for sensing blood oxygen, a temperature sensor for sensing human body temperature, a pulse sensor for sensing beating frequency of pulse, or a respiration and heartbeat sensor for sensing respiration/heartbeat frequency of the human body.

Specifically, the sensing module 11 of this embodiment includes a metal duct embedded with an intracranial pressure (ICP) sensor fixed therein by a fixed glue. The metal duct has a diameter of less than 5 millimeter (e.g. 2.5 mm), a wall thickness of 0.25 mm and an internal cavity radius of 0.75 mm. The sensing module 11 is implanted into the human skull to detect intracranial pressure (ICP) and physiological signals of the brain in the human skull transmitted to the data transmission module 12 in vitro. In order to separate the metal duct from the pressure at the site to be sensed, the metal duct must be in a closed state, and the atmospheric pressure inside the metal duct should be controlled in a normal pressure.

Figure 3:
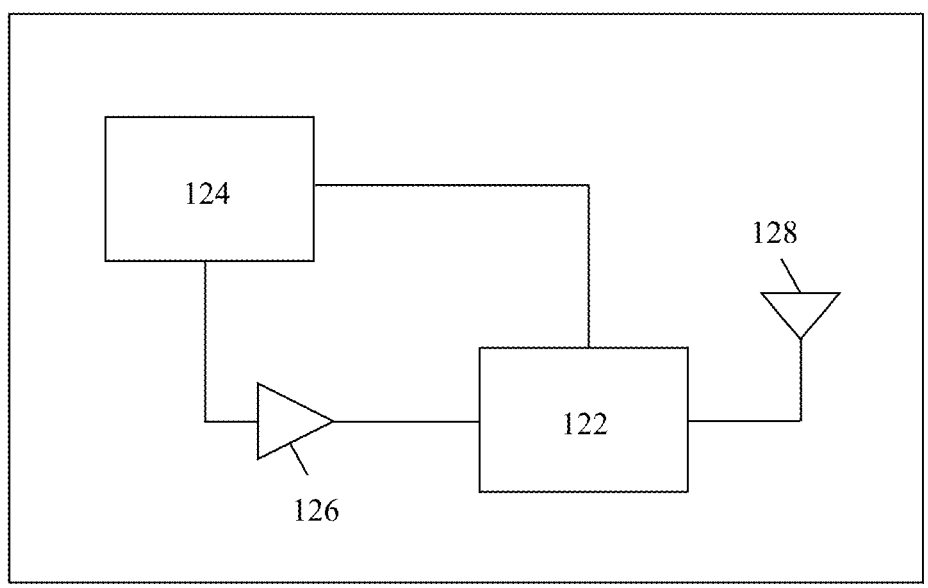
FIG. 3 is a schematic diagram of the data transmission module of the preferred embodiment of the present invention.

Moreover, please refer to FIG. 3, it illustrates a schematic diagram of the data transmission module of the preferred embodiment of the invention. As shown in FIG. 3, the data transmission module 12 of the present embodiment includes a third microprocessor 122, a differential amplifier 124 connected to the third microprocessor 122, a voltage regulating unit 126 connected to the third microprocessor 122 and the differential amplifier 124 respectively, and a data transmission antenna 128 connected to third the microprocessor 122.

The differential amplifier 124 of the data transmission module 12 receives physiological signals transmitted from the sensing module 11 (which can also refer to FIG. 2). Furthermore, the (physiological) signals emitted by the sensing module 11 may be response to physical signals of the outside, such as converting values of temperature or pressure into voltages, analog signals. Therefore, the analog signals need to be amplified through the differential amplifier 124 and converted into digital signals by the third microprocessor 122. The converted digital signals are transmitted to the outside through the data transmission antenna 128 in the form of encrypted packets by the data transmission module 12. Specifically, the data transmission antenna 128 adopted in the present embodiment is not limited to a Bluetooth antenna, a Wi-Fi antenna or a ZigBee antenna.

The voltage regulating unit 126 respectively connected with the third microprocessor 122 and the differential amplifier 124 receives the working voltage transmitted by the power receiving module 13 (which can refer to FIG. 4) and maintains the stability of the working voltage, which is allocated to the third microprocessor 122 and the differential amplifier 124. The resistance of the voltage regulating unit 126 will respond to the changes of input operating voltage of the load (i.e. the microprocessor and the differential amplifier) so that the output voltage is stable. It operates as a variable resistance that automatically adjusts the value of the resistance so that an input voltage of the voltage regulating unit and the voltage division of the load remain the same, and the energy generated by the difference between the output voltage and the input voltage is dissipated in the form of heat.

Figure 4:
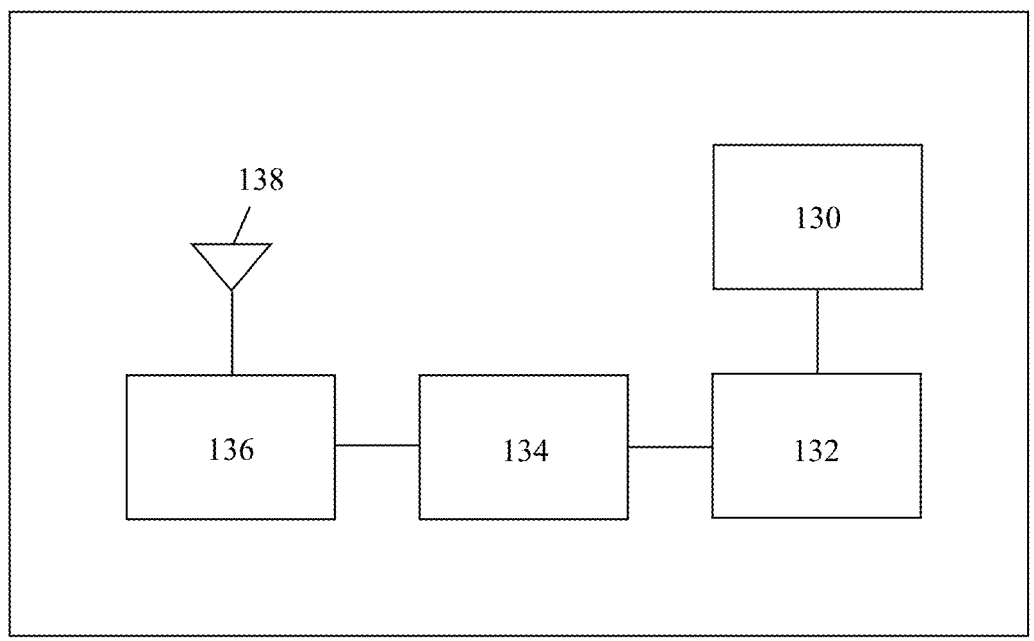
FIG. 4 is a schematic diagram of the power receiving module of the preferred embodiment of the present invention.

Finally, please refer to FIG. 4, it illustrates a schematic diagram of the power receiving module of the preferred embodiment of the invention. As shown in FIG. 4, the power receiving module 13 includes a power receiving antenna 138, an impedance matching unit 136 connected to the power receiving antenna 138, a voltage rectifying unit 134 connected to the impedance matching unit 136, a boost conversion unit 132 connected to the voltage rectifying unit 134, and a power storage unit 130 connected to the boost conversion unit 132.

The power receiving antenna 138 may receive radio frequency signals from an external source and transmit all radio frequency signals to the voltage rectifying unit 134 via the impedance matching unit 136 connected to the power receiving antenna 138. The purpose of using the impedance matching unit 136 is to enable the impedance matching unit 136 to transmit all high frequency microwave signals (herein, RF signals) to the load point (in this case, the voltage rectifying unit 134), and almost no signal is reflected back to the source point (in this case, the power receiving antenna 138), thereby improving power conversion efficiency. The voltage rectifying unit 134 converts the received RF signals into DC voltage through the RF-DC conversion circuit, and then the converted DC voltage is raised to a stable working voltage of 3.0 to 4.5 volts (V) (preferable 3.8 volts) through the boost conversion unit 132 connected with the voltage rectifying unit 134. The stable working voltage are provided for the data transmission module 12 and the sensing module 11, and the excess working voltage can be stored in the power storage unit 130 for subsequent power supply.

The system architecture and connection relationship of the power relay device 20 of the present embodiment will be explained below.

Figure 5:
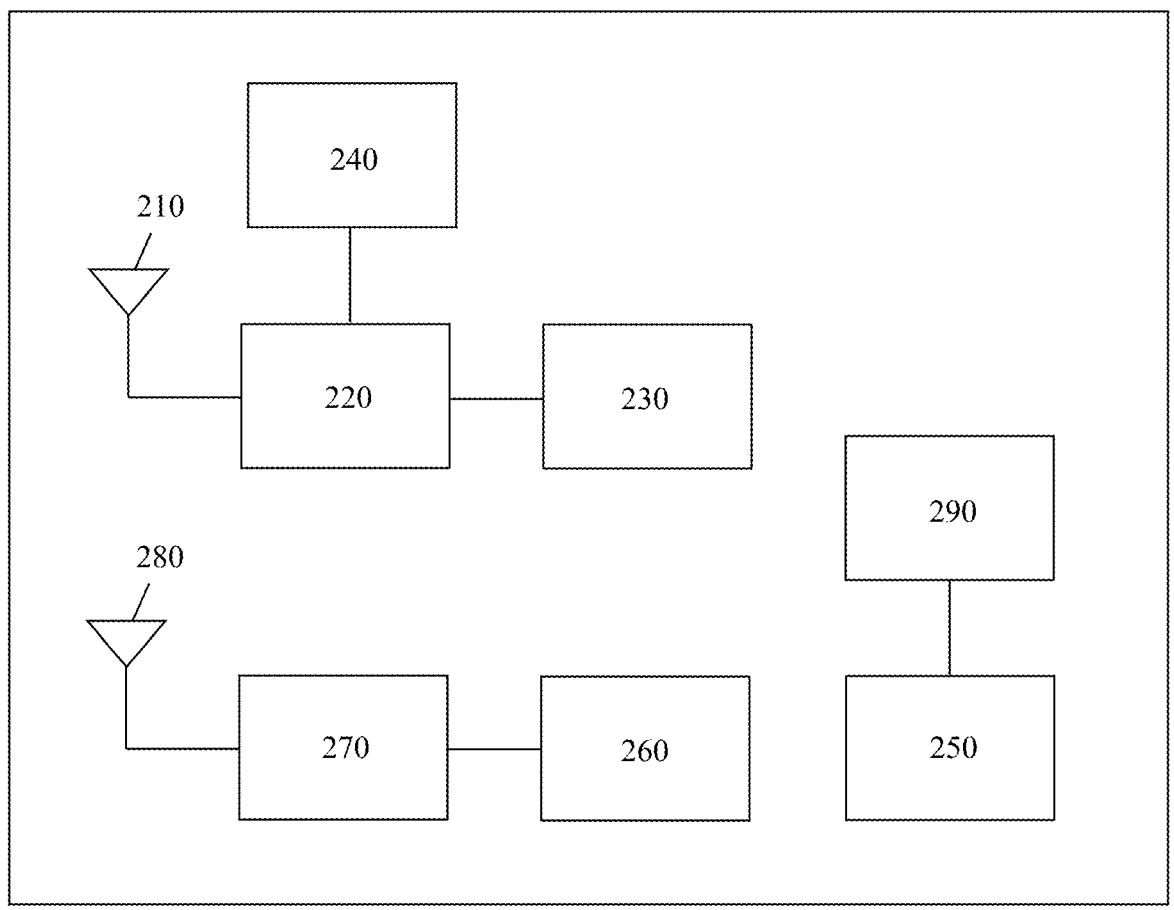
FIG. 5 is a schematic diagram of the power relay device of the preferred embodiment of the present invention.

Please refer to FIG. 5, it illustrates a schematic diagram of the power relay device of the preferred embodiment of the invention. As shown in FIG. 5, the power relay device 20 of the present embodiment includes a data transceiver antenna 210 wirelessly connected to the data transmission module 12 (which can refer to FIG. 5), a first microprocessor 220 connected to the data transceiver antenna 210, a display module 230 connected to the first microprocessor 220, a power emitting antenna 280 wirelessly connected to the power receiving module 13 (which can also refer to FIG. 4), and a power emitting module 260 connected to the power emitting antenna 280. The power emitting module 260 can generate a radio frequency signal with 815 MHz to 5.8 GHz and transmit it to the power receiving module 13.

Specifically, the power relay device 20 of the present embodiment is an independent device connected to the implantable sensing device 10 (which can refer to FIG. 1) in a leadless or adaptor-less manner, and the power relay device 20 can bidirectionally transmit data and power with the implantable sensing device 10. Firstly, taking data transmission as an example, the implantable sensing device 10 can monitor physiological information of the human body (such as intracranial pressure, systolic/diastolic pressure, body temperature, pulse beating frequency or respiration/heartbeat frequency, etc.) through each sensor in the sensing module 11, and transmit the physiological information to the outside through the data transmission antenna 128 in the data transmission module 12. The physiological information is received through the data transceiver antenna 210 included in the power relay device 20. After receiving the physiological information by the data transceiver antenna 210, comparison and conversion of the physiological information is performed by the first microprocessor 220 and the compared and converted results of the physiological information display on the screen through the display module 230. In some embodiments, the first microprocessor 220 can also be connected to a data storage unit 240 that can record the history of all physiological information for subsequent examining and inspecting.

The physiological information of this embodiment is the intracranial pressure (ICP) value detected by the ICP sensor. The display module 230 can select the conventional LCD display module. The data transceiver antenna 210 used in this embodiment is not limited to a Bluetooth antenna, a Wi-Fi antenna or a ZigBee antenna.

On the other hand, the specific mode of operation of power transmission is described as follows. First, the power emitting module 260 in the power relay device 20 generates a radio frequency signal with 815 MHz to 5.8 GHz (preferable 2.4 GHz) and transmits the radio frequency signal to the outside through the power emitting antenna 280 connected to the power emitting module 260. In some embodiments, a power amplifier 270 can be configured between the power emitting module 260 and the power emitting antenna 280. The power amplifier 270 is a radio frequency power amplifier, which can amplify a small radio frequency signal to a sufficient radio frequency power and then feed it to the power emitting antenna 280. The RF signal can be received by the power receiving antenna 138 of the power receiving module 13 in the implantable sensing device 10. After a series process of signal conversion, voltage rectification and voltage amplification are performed by the power receiving module 13, the RF signal can be converted to a working voltage of about 3.8 volts (V) to provide the entire implantable sensing device 10 for use.

In addition, the power relay device 20 may include an AC/DC conversion unit 250 and a battery unit 290. When the power relay device 20 is idle, the AC/DC conversion unit 250 can be connected with the supply mains to charge the battery unit 290 in the device 20. When the power relay device 20 operates, the battery unit 290 can provide the working voltage of the power relay device 20.

Finally, the system architecture and its connection relationship of the external monitoring device 30 of this embodiment will be further explained.

Figure 6:
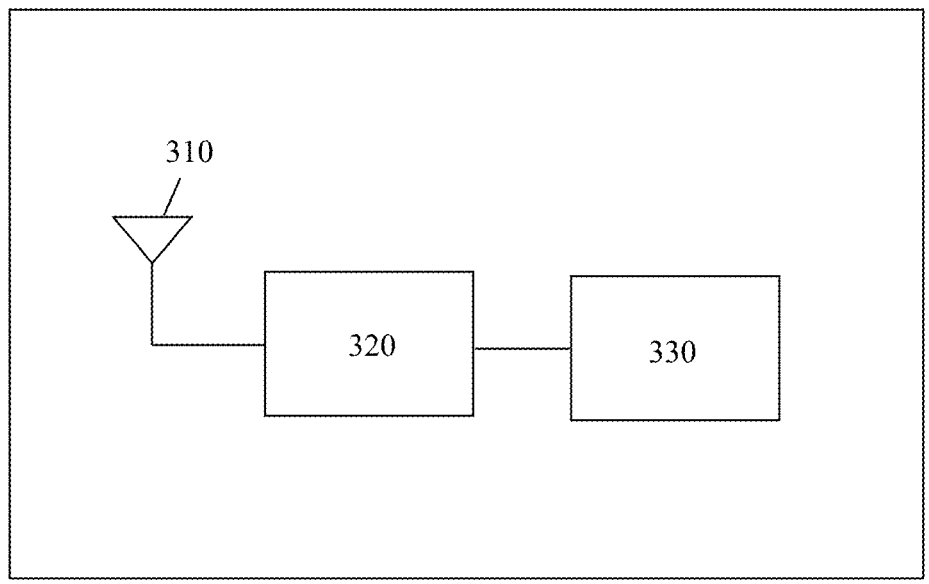
FIG. 6 is a schematic diagram of the external monitoring device of the preferred embodiment of the present invention.

Please refer to FIG. 6, it illustrates a schematic diagram of the external monitoring device of the preferred embodiment of the invention. As shown in FIG. 6, the external monitoring device 30 of the present embodiment is wirelessly connected to the power relay device 20 (with reference to FIG. 5). The external monitoring device 30 comprises a data receiving unit 310 wirelessly connected to the data transceiver antenna 210 of the power relay device 20, a second microprocessor 320 connected to the data receiving unit 310, and a display unit 330 connected with the second microprocessor 320. The data receiving unit 310 receives the at least one physiological signal transmitted by the data transceiver antenna 210, then performs comparison and conversion of the physiological information by the second microprocessor 320, and displays the physiological information on the screen through the display unit 330. Thus, the third-party user can wirelessly, remotely monitor the physiological information measured by the implantable sensing device 10, thereby increasing the scope of subsequent applications.

Figure 7:
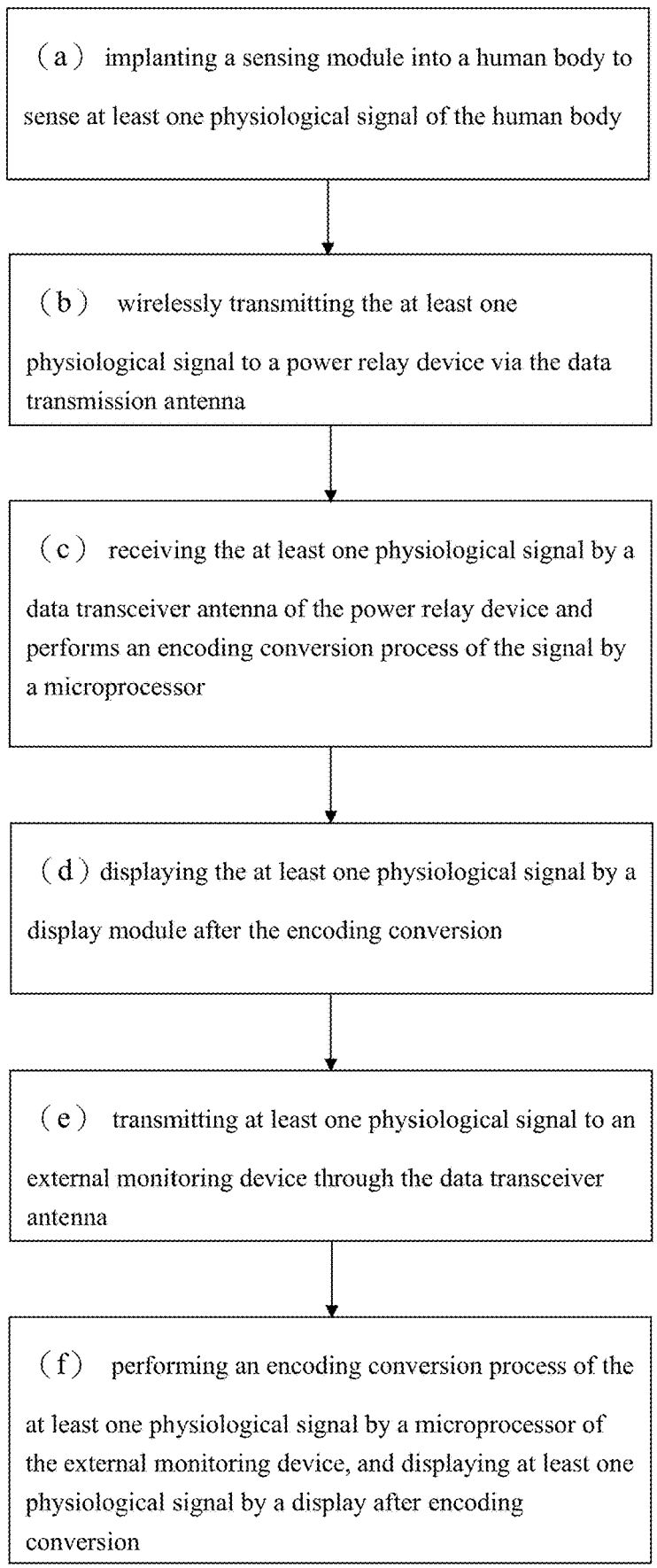
FIG. 7 is a flow chart of a signal transmission method for a physiological signal wireless transmission system according to a preferred embodiment of the present invention.

In addition to the above-mentioned physiological signal wireless transmission system, the invention also proposes a signal transmission method and a wirelessly charging method for the physiological signal wireless transmission system. Firstly, referring to FIG. 7, it illustrates a flow chart of a signal transmission method for a physiological signal wireless transmission system according to a preferred embodiment of the present invention. As shown in FIG. 7, the signal transmission method of the system includes the following steps:

First, the step (a) is performed by implanting a sensing module 11 into a human body to sense at least one physiological signal of the human body. The sensing module 11 comprises at least one sensor, and the at least one sensor may be an intracranial pressure (ICP) sensor for detecting human intracranial pressure, a blood pressure sensor for detecting systolic/diastolic pressure of human body, a blood oxygen sensor for detecting human blood oxygen, a temperature sensor for detecting human body temperature, a pulse sensor for detecting human pulse beat frequency or a respiration and heartbeat sensor for detecting the respiration/heartbeat frequency of the human body.

At least one physiological signal includes intracranial pressure, systolic/diastolic pressure, body temperature, pulse beating frequency, or respiration/heartbeat frequency, etc. In this embodiment, the intracranial pressure (ICP) sensor is implanted into the human brain to measure a value of the intracranial pressure as a physiological signal.

Then, in the step (b), various analog signals (physiological signals) are amplified through a differential amplifier 124 of a data transmission module 12, and the analog signals are converted into digital signals by the third microprocessor 122, and then wirelessly transmits the at least one physiological signal to a power relay device 20 via the data transmission antenna 128.

Further, in the step (c), a data transceiver antenna 210 of the power relay device 20 receives the at least one physiological signal and performs an encoding conversion process of the signal by a first microprocessor 220. Then, in the step (d), a display module 230 displays the at least one physiological signal after the encoding conversion.

In addition, in the step (e), at least one physiological signal can be transmitted to an external monitoring device 30 through the data transceiver antenna 210 of the power relay device 20. Finally, in the step (f), the data receiving unit 310 of the external monitoring device 30 receives the physiological signal, and performs an encoding conversion process of the at least one physiological signal by a second microprocessor 320. Then, a display unit 330 is used to display at least one physiological signal after encoding conversion.

Figure 8:
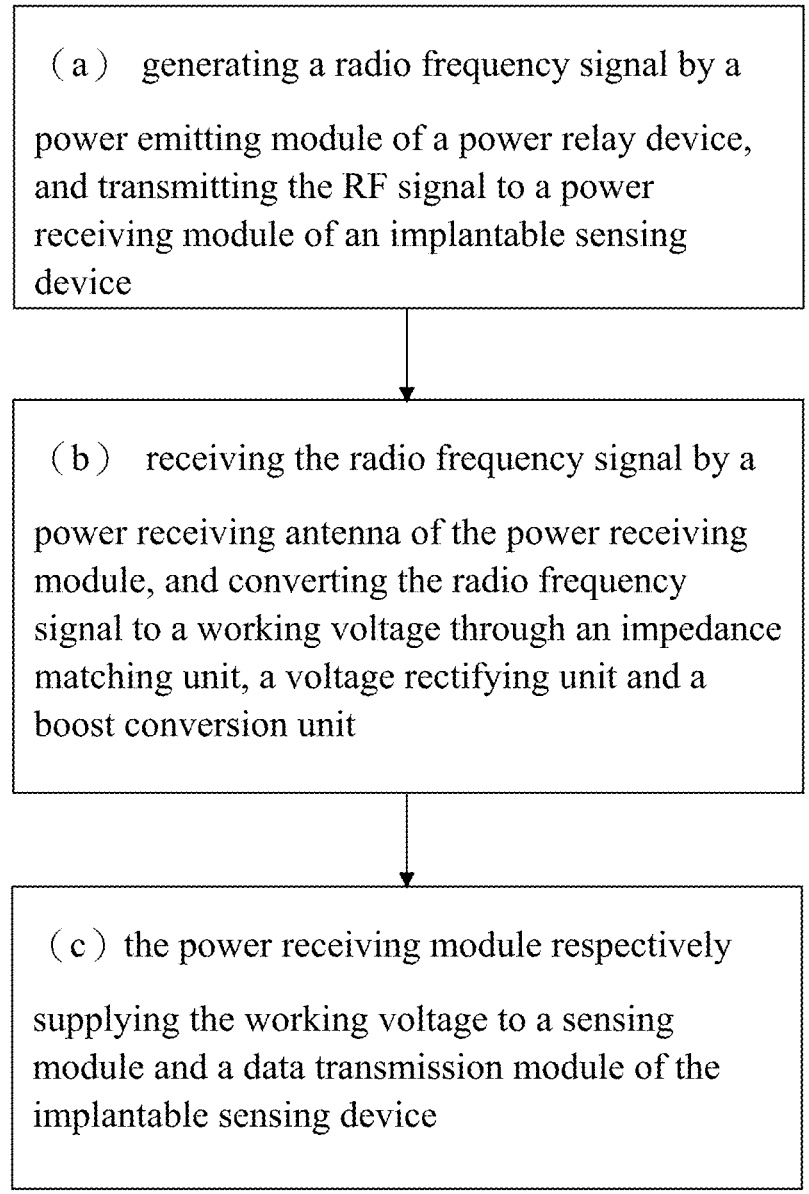
FIG. 8 is a flow chart of a wirelessly charging method for a physiological signal wireless transmission system according to a preferred embodiment of the present invention.

Finally, referring to FIG. 8, it illustrates a flow chart of a wirelessly charging method for a physiological signal wireless transmission system according to a preferred embodiment of the present invention. As shown in FIG. 8, the wirelessly charging method of the system includes the following steps:

Firstly, in the step (a), a power emitting module 260 of a power relay device 20 generates a radio frequency signal with 815 MHz to 5.8 GHz (preferable 2.4 GHz), and transmits the RF signal to a power receiving module 13 of an implantable sensing device 10 through a power transmission antenna 280. Then, in the step (b), a power receiving antenna 138 of the power receiving module 13 receives the radio frequency signal, and converts the radio frequency signal to a working voltage of 3.0 to 4.5 volts (V) (preferable 3.8 volts) through an impedance matching unit 136, a voltage rectifying unit 134, and a boost conversion unit 132. Finally, in the step (c), the power receiving module 13 respectively supplies the working voltage to the sensing module 11 and the data transmission module 12 of the implantable sensing device 10 to complete the charging of the physiological signal wireless transmission system 1.

Through the above-mentioned steps, the power relay device can be connected to the implantable sensing device in a wire-less or adapter-less manner, and can also be used for two-way transmission of physiological information and energy with the implantable sensing device, and the information can also be wirelessly transmitted to the remote external monitoring device, thereby effectively avoiding the risk caused by current magnetic field excited from the sensing device while the MRI scanning is performed.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure. While the preferred embodiment of the invention has been illustrated and described, it will be appreciated that various changes can be made therein without departing from the spirit and scope of the invention.

What is claimed is:

1. A physiological signal wireless transmission system compatible with a magnetic resonance (MR) system, comprising an implantable sensing device and a power relay device wirelessly coupled to said implantable sensing device;
   wherein said implantable sensing device includes:
   a sensing module having a closed metal duct embedded with at least one sensor to sense at least one physiological signal;
   wherein the at least one sensor comprises an intracranial pressure (ICP) sensor, a blood pressure sensor, a blood oxygen sensor, a temperature sensor, a pulse sensor, a respiration, a heartbeat sensor or a combination thereof;
   a data transmission module coupled to said sensing module to transmit said at least one physiological signal; and
   a power receiving module coupled to said sensing module and said data transmission module to provide a working voltage to said sensing module and said data transmission module;
   wherein said power relay device includes:
   a data transceiver antenna wirelessly coupled to said data transmission module to receive and transmit said at least one physiological signal;
   a first microprocessor coupled to said data transceiver antenna;
   a display module coupled to said first microprocessor to display said at least one physiological signal;
   a power emitting antenna wirelessly coupled to said power receiving module; and
   a power emitting module coupled to said power emitting antenna to generate a radio frequency signal with 815 MHz to 5.8 GHz;
   wherein said power receiving module includes:
   a power receiving antenna to receive said radio frequency signal;
   an impedance matching unit coupled to said power receiving antenna;
   a voltage rectifying unit coupled to said impedance matching unit; and
   a boost conversion unit coupled to the voltage rectifying unit;
   wherein the boost conversion unit raises said working voltage to a range of 3.0 to 4.5 volts;
   wherein said data transmission module includes a voltage regulating unit to receive the working voltage transmitted by the power receiving module.

2. The system of claim 1, further comprising an external monitoring device wirelessly coupled to said power relay device, wherein said external monitoring device comprises:
   a data receiving unit wirelessly coupled to said data transceiver antenna to receive said at least one physiological signal;
   a second microprocessor coupled to said data receiving unit; and
   a display unit coupled to said second microprocessor to display said at least one physiological signal.

3. The system of claim 1, wherein said data transmission module includes:
   a third microprocessor;
   a differential amplifier coupled to said third microprocessor;
   the voltage regulating unit coupled to said third microprocessor and said differential amplifier respectively, and
   a data transmission antenna coupled to said third microprocessor.

4. The system of claim 1, wherein said power receiving module further includes:
   a power storage unit coupled to said boost conversion unit to store said working voltage.

5. The system of claim 1, wherein said power relay device further includes a data storage unit coupled to said first microprocessor and a power amplifier coupled to said power emitting module and said power emitting antenna respectively.

6. The system of claim 1, wherein said data transceiver antenna is a Bluetooth antenna, a Wi-Fi antenna or a ZigBee antenna.

7. The system of claim 3, wherein said data transmission antenna is a Bluetooth antenna, a Wi-Fi antenna or a ZigBee antenna.

8. A signal transmission method based-on said physiological signal wireless transmission system of claim 1, comprising:
   (a) implanting said sensing module into a human body to sense at least one physiological signal of said human body;
   (b) wirelessly transmitting said at least one physiological signal by said data transmission module to said power relay device;

(c) receiving said at least one physiological signal by said data transceiver antenna of said power relay device, and performing an encoding conversion process of said at least one physiological signal by said first microprocessor;

(d) displaying said at least one physiological signal after said encoding conversion process by said display module;

(e) transmitting said at least one physiological signal to an external monitoring device by said data transceiver antenna; and (f) performing a second encoding conversion process of said at least one physiological signal by a second microprocessor of said external monitoring device, and displaying said at least one physiological signal by said display unit after said second encoding conversion process.

9. A wirelessly charging method based-on said physiological signal wireless transmission system of claim 1, comprising:

(a) generates a radio frequency signal with 815 MHz to 5.8 GHz by said power emitting module of said power relay device, and transmitting said radio frequency signal to said power receiving module;

(b) receiving said radio frequency signal by said power receiving antenna of said power receiving module, and converting said radio frequency signal to a working voltage of 3.0 to 4.5 volts (V) by an impedance matching unit, a voltage rectifying unit and a boost conversion unit; and (c) supplying said working voltage said power receiving module to said sensing module and said data transmission module of said implantable sensing device respectively.

* * * * *